(12) United States Patent
Reinmüller

(10) Patent No.: US 7,807,656 B2
(45) Date of Patent: Oct. 5, 2010

(54) PHARMACEUTICAL APPLICATIONS OF HYALURONIC ACID PREPARATIONS

(76) Inventor: Johannes Reinmüller, Schöne Aussicht 46, 65193 Wiesbaden (DE)

( * ) Notice: Subject to any disclaimer, the term of this patent is extended or adjusted under 35 U.S.C. 154(b) by 924 days.

(21) Appl. No.: 10/495,200

(22) PCT Filed: May 22, 2003

(86) PCT No.: PCT/EP02/12659

§ 371 (c)(1), (2), (4) Date: May 11, 2004

(87) PCT Pub. No.: WO03/041723

PCT Pub. Date: May 22, 2003

(65) Prior Publication Data

US 2005/0187185 A1 Aug. 25, 2005

(30) Foreign Application Priority Data

Nov. 12, 2001 (DE) ............... 101 55 440
Mar. 7, 2002 (DE) ............... 102 09 966

(51) Int. Cl.
*A61K 31/728* (2006.01)
*C07H 5/04* (2006.01)
*C08B 37/00* (2006.01)

(52) U.S. Cl. ............... 514/54; 536/55.1

(58) Field of Classification Search ............... 514/54
See application file for complete search history.

(56) References Cited

U.S. PATENT DOCUMENTS

| | | | |
|---|---|---|---|
| 4,141,973 A | 2/1979 | Balazs | 424/180 |
| 4,636,524 A | 1/1987 | Balazs et al. | 514/781 |
| 4,946,832 A | 8/1990 | Goode et al. | 514/53 |
| 4,965,071 A | 10/1990 | Kawan | 424/401 |
| 5,256,140 A | 10/1993 | Fallick | 604/51 |
| 5,290,271 A * | 3/1994 | Jernberg | 604/891.1 |
| 5,679,655 A | 10/1997 | Gallina | 514/54 |
| 5,914,314 A | 6/1999 | Falk et al. | 514/11 |
| 6,048,844 A * | 4/2000 | Falk et al. | 514/54 |
| 6,194,392 B1 | 2/2001 | Falk et al. | 514/54 |
| 6,465,626 B1 * | 10/2002 | Watts et al. | 536/20 |
| 6,482,806 B1 * | 11/2002 | Koyama et al. | 514/54 |
| 6,824,793 B1 * | 11/2004 | O'Hagan et al. | 424/491 |
| 2002/0025921 A1 * | 2/2002 | Petito et al. | 514/2 |
| 2002/0132790 A1 * | 9/2002 | Benedetti et al. | 514/57 |

FOREIGN PATENT DOCUMENTS

| | | | |
|---|---|---|---|
| CN | 0000111241 | | 7/2000 |
| DE | 195 20 575 A1 | | 12/1996 |
| DE | 199 23 829 A1 | | 11/2000 |
| EP | 0270317 | * | 8/1988 |
| EP | 0 838 219 A1 | | 9/1997 |
| JP | 19890321726 | | 12/1989 |
| WO | WO 90/14095 | | 11/1990 |
| WO | WO90/14095 | * | 11/1990 |
| WO | WO 93/12801 | | 7/1993 |
| WO | WO96/06622 | * | 3/1996 |
| WO | WO9830207 | * | 7/1998 |

OTHER PUBLICATIONS

Geronemus et. al. J. Am. Acad. Dermatol. 41(4), 1999, 624-634.*
Gressner et. al. J. Clin. Chem. Clin. Biochem., 27(3), 1989, Abstract.*
Xu et. al. International Journal of Biological Macromolecules, 30, 2002, 151-160.*
The Merck Manual of Diagnosis and Therapy, Seventeenth Edition, published 1999 by Merck Research Labortories, pp. 1293-1294.*
Pinter et al., "Short-term effect of amantadine sulphate on motor performance and reaction time in patients with idiopathic Parkinson's disease" Journal of Neural Transmission (1999) vol. 106, pp. 711-724.*
Ramsey et al., "Herpes Simplex Virus Pneumonia" Annals of Internal Medicine (1982) vol. 97 pp. 813-820.*
Saliba, Jr., Michael J., "Heparin in the treatment of burns: a review," *BURNS*, vol. 27, (2001) pp. 349-358.
Martin, P. H. et al., "Use of liposuction and saline washout for the treatment of extensive subcutaneous extravasation of corrosive drugs," *British Journal of Anaesthesia*, vol. 72, (1994) pp. 702-704.

* cited by examiner

*Primary Examiner*—Eric S Olson
(74) *Attorney, Agent, or Firm*—Ping Wang; Morris, Manning & Martin, LLP

(57) ABSTRACT

The invention relates to novel applications of pharmaceutical compositions containing preferably long-chain hyaluronic acids which are cross-linked or not cross-linked, and conventional adjuvants and/or supporting materials.

1 Claim, No Drawings

PHARMACEUTICAL APPLICATIONS OF HYALURONIC ACID PREPARATIONS

CROSS-REFERENCE TO RELATED APPLICATIONS

This application is a national stage application of PCT/EP02/12659, filed May 22, 2003, which claims priority to foreign applications DE10155440.1, filed Nov. 12, 2001, and DE10209966.9, filed Mar. 7, 2001.

The present invention relates to novel applications of pharmaceutical compositions which comprise crosslinked or uncrosslinked and preferably long-chain hyaluronic acid as well as customary pharmaceutical auxiliary and/or carrier substances. One aspect relates to the use of a composition which comprises hyaluronic acid associated with heparin for releasing heparin in a delayed manner, for example in connection with treating wounds, scars and keloids, for inhibiting blood coagulation or for relieving pain. Another aspect of the invention relates to the use of a hyaluronic acid-comprising pharmaceutical composition for treating viral infections, in particular for treating an infection with herpesviruses. Yet another aspect of the invention relates to the use of a hyaluronic acid-comprising pharmaceutical composition as an analgesic, in particular for administration in the region of nerve endings. Finally, yet another aspect of the invention relates to the use of a hyaluronic acid-comprising pharmaceutical composition for tautening skin, in particular for reducing the size of wrinkles in the facial region in a long-lasting manner.

Hyaluronic acid is an unsulfated glycosaminoglycan which is found in the human body in synovial fluid and in extracellular matrices. It is frequently used as a building block for biocompatible and biologically degradable polymers in a variety of medical applications.

European patent 0619737 relates to a pharmaceutical composition for the nontopical treatment of wounds, scars and keloids, which composition comprises one or more crosslinked glycosaminoglycan(s) and customary pharmaceutical auxiliary and/or carrier substances. Hyaluronic acid and heparin are mentioned, inter alia, as being examples of glycosaminoglycans. The publication also discloses the combination of crosslinked glycosaminoglycans and other pharmaceutical active compounds such as antibiotics.

It has now been found, surprisingly, that a pharmaceutical composition which comprises crosslinked or uncrosslinked hyaluronic acid, preferably long-chain hyaluronic acid, associated with heparin, preferably with short-chain heparin which has a chain length of, for example, from 5 to 10 saccharide units, is suitable for releasing heparin in a delayed manner, for example for local applications, such as for treating wounds, scars or keloids, or for relieving pain, and also for systemic applications, such as inhibiting blood coagulation. In addition to its own advantageous physiological effects, the hyaluronic acid serves as a matrix for enabling heparin to be released in a controlled manner. The rate of release can be controlled by way of the degree of crosslinking, and the nature of the crosslinking, of the hyaluronic acid as well as the nature of the heparin and its association with the hyaluronic acid.

The composition according to the invention has an inhibitory effect on keloid formation, particularly when it is administered nontopically (within the lesion). Administration of the compositions according to the invention can be used to successfully treat all types of scar, including deep scar formations in connective tissue, such as Dupuytren's disease of the palmar surfaces or what is termed plastic induration of the penis, which develop without any preceding trauma (cross-section).

The composition exhibits a number of advantages as compared with known preparations. Thus, it is possible to administer it by injection in a manner which is to a large extent pain-free. In addition, no local hyperintensive reactions and no unwanted systemic side-effects occur. Another advantage is its biological degradability in the body. An advantage as compared with the compositions disclosed in European patent 0 619 737 is, in particular, that the rate at which the heparin is released can be varied in dependence on the application, e.g. in accordance with the nature of the hyaluronic acid matrix employed and of the heparin employed. Thus, it is possible to achieve what is essentially a constant rate of release of the active compound for a relatively long period of time, e.g. 1 week or more, both in connection with local applications and in connection with systemic applications.

Furthermore, the composition is also suitable for other known pharmaceutical uses of heparin, including both systemic and local uses, e.g. for inhibiting blood coagulation. In addition, surgical methods can also be used to administer the composition in the form of an implant.

It was possible to administer the preparation subcutaneously to patients, for the purpose of thrombosis prophylaxis, in a manner which was to a large extent pain-free. The administration was repeated several times at intervals of 7 days.

The hyaluronic acid can be used in uncrosslinked or crosslinked, e.g. covalently or noncovalently crosslinked, form. The crosslinked hyaluronic acid can be prepared in a manner which is known per se. In this connection, the covalent crosslinking is in general effected by crosslinking with bifunctional reactive agents, such as glutaraldehyde or carbodiimide; by way of bifunctional amino acids, e.g. lysine, protamines or albumins. However, it is also possible, for example, for crosslinkings to be produced by way of an amide bond. Other reagents which are suitable for covalently crosslinking hyaluronic acid are ethylene glycol diglycidyl ether, 1,4-butanediol diglycidyl ether, divinylsulfone, photo-crosslinking reagents, such as ethyl eosin, and hydrazides, such as bishydrazide compounds, trishyrazide compounds and polyvalent hydrazide compounds. It is furthermore also possible to use hyaluronic acid derivatives which are esterified intramolecularly and/or intermolecularly.

Particular preference is given to crosslinking in a noncovalent manner, using multiply charged metal ions, such as iron, copper, zinc, calcium, magnesium, barium and other chelating metal ions.

Hyaluronic acid is commercially available in the crosslinked state (e.g. Hylon® and Hylagel®, a crosslinked hyaluronic acid from Biomatrix, N.J., USA; for the preparation cf. U.S. Pat. No. 4,713,448 and U.S. Pat. No. 4,605,691 as well, APC® from Fidia, Incert® from Anika Therapeutics or Intergel® from LifeCore) and can then be used in accordance with the invention after having been associated with heparin.

In a particularly preferred embodiment, long-chain hyaluronic acid (molecular weight preferably between $10^4$ and $10^6$ Da, in particular between $10^5$ and $10^6$ Da) is used; it is then possible for the degree of crosslinking to remain low. Short-chain hyaluronic acid is also suitable when the degree of crosslinking is higher, with it also being possible to use molecules having a low chain length of only a few, e.g. $\geq 10$, preferably $\geq 20$, saccharide units.

The association of the heparin with the hyaluronic acid can be effected covalently or noncovalently, e.g. by means of chemical crosslinking or by means of chelate formation, as explained above. Physiologically tolerated multiply charged metal ions, such as $Mg^{2+}$, $Ca^{2+}$, $Zn^{2+}$, $Fe^{2+}$ or $Fe^{3+}$, are preferably used for the chelate formation.

The pharmaceutical compositions according to the invention preferably comprise the hyaluronic acid in quantities of from 0.01 to 20% by weight, based on the total pharmaceutical composition, in particular in a quantity of from 0.01 to 5% by weight and, particularly preferably, in a quantity of from 0.01 to 1% by weight.

The proportion of heparin in the compositions can be varied within wide ranges and depends on the size and nature (e.g. crosslinked and uncrosslinked) of the heparin and its association with the hyaluronic acid and the envisaged nature and duration of the application. In general, the proportion is in the range of from 0.1 to 20% by weight, based on the total pharmaceutical composition, in particular of from 0.5 to 10% by weight, and particularly preferably of from 1 to 5% by weight. Depending on the application, the heparin can be present in long-chain or short-chain, crosslinked or uncrosslinked form. Preference is given to using short-chain heparin having a size of 5-50, in particular 5-10, saccharide units.

The pharmaceutical compositions according to the invention can be present in the form of preparations which can be administered by means of injection or surgical interventions and, in particular, in the form of injectable or implantable gels or solutions, preferably having a water content of from 60 to 99% by weight, or else as an anhydrous precursor, e.g. lyophilized powder in pulverulent form. The pharmaceutical auxiliary and carrier substances which can be used for this purpose are customary substances which are suitable for the application according to the invention and which are compatible with hyaluronic acid and heparin. The preferred carrier substance is water or an aqueous buffer solution.

Examples of pharmaceutical auxiliary substances which the pharmaceutical compositions according to the invention can comprise are agents for adjusting the pH, stabilizing agents, antioxidants, solubilizers, penetration-promoting agents, preservatives and/or gelatinizing agents, as are customarily used in compositions of this nature. They are employed in the quantities which are customary in preparations of this nature.

In addition to the true active compounds hyaluronic acid plus heparin, the pharmaceutical compositions according to the invention can, where appropriate, also comprise additional pharmaceutical active compounds which are compatible with the hyaluronic acid and the heparin within the context of the application, e.g. active compounds for treating skin diseases (dermatoses), antibiotics, e.g. gentamycin, vancomycin, penicillins or cephalosporins, sulfonamides, disinfectants, hormones (e.g. corticoids) and hormone derivatives (e.g. cortisol), local anesthetics, e.g. of the lidocaine or novocaine type, vasoactive substances for vascular constriction (avoidance of hemorrhages), adrenaline, enzymes, such as hyaluronidase, interleukins, growth factors, e.g. EGF, PDGF or IGF, skin care agents and/or blood flow-promoting (hyperemizing) agents. The additional active compounds can, where appropriate, be associated with the hyaluronic acid, e.g. by means of covalent or noncovalent interactions.

In a preferred application according to the invention in the form of an injection, the preparations can comprise local anesthetics, e.g. for the purpose of avoiding pain when puncturing with the injection needle.

The compositions according to the invention can be produced in a well-known manner which is customary per se for producing compositions of this nature. In this connection, the sequence in which the individual constituents are mixed is as a rule not critical.

The nature, dose and frequency of the administration of the composition according to the invention, as well as its constitution (e.g. viscosity, degree of crosslinking, content of active compound, etc.) depend, in particular, on the nature and severity of the disease as well as on the state of health of the patient and the condition of the site of administration, e.g. the condition and the sensitivity of a scar and of the skin or of a wound following a surgical intervention. If the compositions according to the invention are administered in the form of preparations which can be applied topically, the administration then as a rule conforms with the conditions which are customary for compositions of this nature.

The nature of the treatment, and the frequency of the application, also depend, in particular, on the individual response of the persons to be treated. Gels or solutions are preferably applied at intervals of from several days up to one or two months, in particular of from approx one to two weeks.

If the compositions according to the invention are administered intralesionally in the form of injectable gels, this then preferably takes place by injection with the aid of fine needles and using compression-resistant syringes. However, the gels according to the invention can also be shot in transdermally using pressure devices; pressure devices as are known in medicine for such administration can be used for this purpose. Certain preparations can also be administered systemically, i.e. into the blood circulation or into body cavities, for example following surgical intervention. Implantable compositions are preferably present in the form of viscous gels or solutions, i.e. what are termed instillation solutions.

As a result of its association with long-chain hyaluronic acid, uncrosslinked, and even short-chain, heparin can be administered, as an active compound, by injection. The compositions according to the invention prevent the rapid removal of the heparin from the site of action which would otherwise take place in the absence of its association with hyaluronic acid. Depending on the breakdown of the hyaluronic acid matrix, and on the nature of its bonding, the heparin remains active at the site of administration, e.g. in the keloid tissue, for days, weeks or months. Particular preference is given to the duration of action being 5-20 days, e.g. approx. 1-2 weeks.

An advantage of the preferred preparations according to the invention, e.g. in the form of injectable or implantable gels and their administration, is also that no additional hygienic measures whatsoever are required after the injection sites or the surgical sutures have healed. It is possible to treat all body regions equally and the mobility of the patient is not restricted by dressings. Treatment with the preparations according to the invention can prevent the appearance or reappearance of keloids, thereby demonstrating the prophylactic effect of these preparations.

Another application form for preventing keloids or contracted scars is that of administering anhydrous compositions (e.g. as a lyophilisate) to fresh wounds or body cavities in the form of wound powder. In this connection, the powder is sprinkled into the open wound or wound cavity before the wound is closed. The wound is then closed by means of sutures, clips or the like. In the wound, the powder absorbs water from the tissue, and then corresponds to the preparation according to the invention in the form of a gel, or itself constitutes a preparation according to the invention.

In order to prevent unwanted adhesions, compositions in powder form or gel form can also be introduced into large body cavities, for example into the abdominal cavity or thoracic cavity, during a surgical operation on the intestine or on the lung, into the pericardium or by way of indwelling drainages following surgical operations. In the case of inflammatory discharges into large body cavities, the preparation according to the invention can also be introduced by way of the indwelling cannula following puncture and evacuation of the discharge.

The preparation according to the invention can also be introduced into externally accessible cavities and passageways of the body, for example into the main nasal cavities and paranasal sinuses or nasal meatus, or into the tear ducts, for the purpose of preventing scarred adhesions, possibly on a suitable support (e.g. tampon) as well.

Novel applications of pharmaceutical compositions which comprise crosslinked or uncrosslinked hyaluronic acid as active compound constitute yet another aspect of the invention. The reader is referred to the above comments with regard to the hyaluronic acid content of these compositions and their administration forms.

In a first aspect, these compositions are intended for treating viral infections, for example in connection with treating infections with neurotropic viruses, such as herpesviruses, e.g. herpes simplex or herpes zoster. The compositions can be administered locally or systemically depending on the nature of the viral infection. The composition is preferably used for treating dermal or mucosal herpes infections, for example herpes labialis or herpes genitalis. Other preferred areas of application are the treatment of infections with hepatotropic viruses, such as hepatitis viruses, e.g. hepatitis A, B or C viruses, the treatment of infections with immunotropic viruses, e.g. HIV or cytomegalovirus, or the treatment of infections with other neutrotropic viruses, e.g. polio. It is furthermore also possible to treat infections with other viruses which cause diseases of the eyes, e.g. epidemic keratoconjunctivitis, or of the airways, e.g. colds, nasal catarrh or influenza. Examples of these viruses are rhinoviruses and influenza viruses. In some cases, a local, e.g. topical or transdermal administration is preferred. Other preferred administration forms are opthalmological compositions or compositions for nasal administrations, e.g. drops, sprays and inhalable aerosols. On the other hand, the composition can also be administered systemically, e.g. by means of intravenous injection, or orally as a solution for drinking or rinsing, e.g. for controlling infections of the gastric and intestinal tract or of the thorax. Particular preference is given to a single or repeated prophylactic administration prior to the onset of an acute disease.

Surprisingly, it was found that, when the composition in the form of a gel was administered by intradermal or subdermal injection into the affected region in patients suffering from recurring herpes labialis, it was possible, at least to a large extent, to prevent the onset of the infection. After the compositions had been administered, the patients were free from skin eruptions. Administration in the prodromal stage was particularly effective in connection with the onset of pruritus. Where appropriate, the administration of the composition prophylactically can be repeated at relatively large time intervals, for example of 3 months.

Another application of the hyaluronic acid-comprising compositions is that of using them as analgesics, preferably as analgesics which act peripherally, in particular for administration in the region of nerve endings, e.g. of injured nerve endings, for example following incision wounds. In this connection, the administration can, for example, be effected locally by injection, as previously described. In several cases, administration of the composition into surgical wounds, for example as a powder, gel or solution prior to wound closure, resulted in considerable pain alleviation and also in a substantial decrease in the requirement for additional peripheral or central analgesics.

Yet another application of the hyaluronic acid-comprising compositions is that of tautening skin. Surprisingly, it was found that, when the compositions were administered, it was possible to achieve a discernible effect which was long-lasting, i.e. which lasted over a period of at least six months and, in particular, over a period of from one to several years. Thus, the forehead wrinkles of several patients were visibly reduced one year after administering the composition. The compositions are consequently suitable for use as "lift serum" for tautening facial skin and can contribute to avoiding surgical interventions for the purpose of facial tautening. The administration is preferably transdermal, e.g. by means of injection or by using one of the previously described transdermal administration systems, and can be effected in a punctate manner and/or extensively on the skin regions to be tautened.

Hyaluronic acid can also be added to infiltration solutions which are injected into the tissue prior to a liposuction. These infiltration solutions are usually isotonic or hypotonic salt solutions which can contain additives, for example blood vessel-contracting and/or pain-reducing additives, such as noradrenaline, adrenaline, lidocaine, prilocalne, bicarbonate, corticosteroids, etc. Hyaluronic acid (crosslinked and/or uncrosslinked hyaluronic acid) is advantageously added to these solutions at concentrations of from 0.001 to 1.0% (wt/vol), preferably of from 0.01 to 0.5% (wt/vol), e.g. of about 0.025% (wt/vol). It was found that adding the hyaluronic acid mechanically facilitates the process of liposuction, i.e. manipulating the suction curette, which is moved through the adipose tissue, requires less energy input. Furthermore, structures in the adipose tissue which are worth conserving, such as blood vessels, nerves or connective tissue bands, are spared. Adding the hyaluronic acid also makes the process of liposuction markedly more atraumatic when compared with the conventional procedure. Finally, adding the hyaluronic acid to the infiltration solution improves the flow properties of the adipose tissue aspirate such that it is possible to use a lower negative pressure. This also leads to a reduction in the tissue trauma. All in all, adding hyaluronic acid to the infiltration solution protects the remaining adipose tissue in the body and results in the adipose tissue aspirate being withdrawn in a gentler manner. This thereby improves the survival of fat cells in the aspirate.

This is of importance insofar as adipose tissue aspirates can be used as endogenous transplants. Adding hyaluronic acid to the infiltration solution protects the fat cells during withdrawal such that, when transplanted, the transferred tissue is seen to grow more strongly at the recipient site. As a consequence, hyaluronic acid is always particularly preferably added to the infiltration solution when the aspirated adipose tissue is to be transferred to other sites of the body as an autologous transplant. The invention consequently relates to a adipose tissue aspirate which contains hyaluronic acid (crosslinked or uncrosslinked).

Particular preference is given to using the fat aspirate for cosmetic purposes, e.g. for upholstering soft parts in the face. In this case, the aspirate is inserted into the recipient site through thin cannulae having, for example, a diameter of 1-2 mm. The presence of hyaluronic acid in the aspirate or transplant results in the passage of the tissue through the cannula being facilitated. This means less application of pressure for effecting transport through the cannula, less traumatization of the transferred tissue and/or a higher rate of growth of the transferred tissue at the recipient site.

The hyaluronic acid-containing adipose tissue aspirate according to the invention can also be added, after conventional aspiration (without any addition of hyaluronic acid), at relatively high concentration, e.g. 0.1-1% (wt/vol), to the aspirate adipose tissue moiety (fraction) to be transferred, with this likewise resulting in the rate of take of the transferred tissue being increased.

In general, when, for example, transplants of autologous or xenogenic tissues and/or autologous or xenogenic loose or isolated cells, which are not consolidated into a tissue formation, are being transferred through cannula-shaped applicators, an addition of hyaluronic acid (crosslinked and/or uncrosslinked) can improve the survival and/or the growth of the transferred tissue particles or cells.

It is already known that cells which are subsequently intended to be transferred into a recipient organism are treated with hyaluronic acid in a culture. However, it has been found that the concentration of hyaluronic acid in these cultures is not sufficient to ensure a protective effect when the transfer takes place through thin cannulae. It is therefore advisable, before transferring such cells, to effect an addition of hyaluronic acid in accordance with the invention, with the final concentration of hyaluronic acid advantageously being adjusted to from 0.05 to 1.0%, in particular from 0.1 to 0.5% (wt/vol).

Insofar as tissue particles or cells are being transferred into body cavities, hyaluronic acid additionally acts as a lubricant and consequently also as a protective film for transplants, for example in the pericardium, in the pleural cleft or in the peritoneum, since organs are moved against each other in these cavities or cleft spaces. Hyaluronic acid is consequently finally also to be used as a lubricant in the abovementioned cleft spaces.

The invention claimed is:

1. A method for treating influenza or influenza viral infections of the respiratory system in a patient, comprising the steps of:
    (a) providing a pharmaceutical composition comprising crosslinked or uncrosslinked hyaluronic acid and a customary pharmaceutical auxiliary and/or carrier substance, wherein the crosslinked or uncrosslinked hyaluronic acid serves as the only active ingredient in the pharmaceutical composition; and
    (b) administering the pharmaceutical composition in the form of a spray or an inhalable aerosol by means of therapeutic interventions.

* * * * *